(12) United States Patent  
Jacono et al.

(10) Patent No.: US 9,404,911 B2  
(45) Date of Patent: Aug. 2, 2016

(54) INTEGRATED ASSAY DEVICE AND HOUSING

(75) Inventors: Bruce Jacono, San Diego, CA (US); John C. Barry, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 1447 days.

(21) Appl. No.: 12/427,710

(22) Filed: Apr. 21, 2009

(65) Prior Publication Data

US 2009/0263854 A1 Oct. 22, 2009

Related U.S. Application Data

(60) Provisional application No. 61/046,789, filed on Apr. 21, 2008.

(51) Int. Cl.  
*G01N 33/558* (2006.01)  
*G01N 33/487* (2006.01)

(52) U.S. Cl.  
CPC ........ *G01N 33/48778* (2013.01); *G01N 33/558* (2013.01)

(58) Field of Classification Search  
USPC ......... 422/400, 401, 408, 412, 420, 424, 425, 422/429, 430; 435/4, 7.1, 7.92, 7.93, 7.94, 435/287.2, 287.7, 287.8, 287.9, 288.7; 436/514, 518, 169, 170  
See application file for complete search history.

(56) References Cited

U.S. PATENT DOCUMENTS

| D234,189 S | 1/1975 | Hesselgren |
| 4,496,654 A | 1/1985 | Katz et al. |
| 4,518,565 A * | 5/1985 | Boger et al. .................. 422/404 |
| D279,817 S | 7/1985 | Chen et al. |
| D299,744 S | 2/1989 | Bauer |
| 4,818,677 A | 4/1989 | Hay-Kaufman et al. |
| D301,167 S | 5/1989 | Raybould et al. |
| 4,837,373 A * | 6/1989 | Gunkel et al. ................ 422/424 |
| D308,722 S | 6/1990 | Chang et al. |
| D309,012 S | 7/1990 | Vcelka |
| 4,943,522 A | 7/1990 | Eisinger et al. |
| D310,265 S | 8/1990 | Mochnal et al. |
| D315,791 S | 3/1991 | Meyers et al. |
| 4,999,287 A * | 3/1991 | Allen ...................... C12Q 1/26 422/408 |
| D316,298 S | 4/1991 | Morrow |
| D319,103 S | 8/1991 | Chiu |
| 5,087,556 A * | 2/1992 | Ertinghausen ........ B01L 3/5027 422/562 |
| D324,426 S | 3/1992 | Fan et al. |
| 5,118,630 A | 6/1992 | Glaze |
| 5,147,606 A * | 9/1992 | Charlton .......... B01L 3/502753 422/412 |
| D332,834 S | 1/1993 | Hanna et al. |

(Continued)

FOREIGN PATENT DOCUMENTS

WO 00/37939 * 6/2000

OTHER PUBLICATIONS

Jacono et al., "Integrated Assay Device and Housing", Design U.S. Appl. No. 29/310,381, 3 pages (filed Aug. 11, 2008).

*Primary Examiner* — Chris L Chin  
(74) *Attorney, Agent, or Firm* — Judy M. Mohr; Jacqueline F. Mahoney; McDermott Will & Emery LLP

(57) ABSTRACT

A laminated, integrated, analyte assay device and methods of using the device are described. The assay device is useful as an inexpensive, disposable assay device for detecting the presence and/or amount of a particular analyte in a body fluid or other sample.

16 Claims, 6 Drawing Sheets

(56) References Cited

U.S. PATENT DOCUMENTS

| | | |
|---|---|---|
| 5,221,616 A | 6/1993 | Kolb et al. |
| 5,223,220 A | 6/1993 | Fan et al. |
| 5,225,328 A | 7/1993 | Chang |
| 5,234,813 A * | 8/1993 | McGeehan ....... B01L 3/502715 422/404 |
| D341,663 S | 11/1993 | Coulter |
| D342,575 S | 12/1993 | Ashihara et al. |
| 5,268,146 A | 12/1993 | Lawrence et al. |
| D348,521 S | 7/1994 | Meyers et al. |
| D355,493 S | 2/1995 | Gropper et al. |
| 5,415,994 A | 5/1995 | Imrich et al. |
| 5,434,057 A | 7/1995 | Dorian |
| D361,842 S | 8/1995 | Nazareth et al. |
| D369,868 S | 5/1996 | Nazareth et al. |
| 5,536,646 A | 7/1996 | Sand et al. |
| 5,541,069 A | 7/1996 | Mortensen et al. |
| D383,549 S | 9/1997 | Arnett et al. |
| 5,686,315 A | 11/1997 | Pronovost et al. |
| 5,712,172 A | 1/1998 | Huang et al. |
| 5,741,662 A | 4/1998 | Madsen et al. |
| 5,763,262 A | 6/1998 | Wong et al. |
| 5,766,961 A | 6/1998 | Pawlak et al. |
| 5,770,460 A | 6/1998 | Pawlak et al. |
| 5,773,234 A | 6/1998 | Pronovost et al. |
| 5,783,401 A | 7/1998 | Toledano |
| 5,786,220 A | 7/1998 | Pronovost et al. |
| 5,804,452 A | 9/1998 | Pronovost et al. |
| 5,846,751 A | 12/1998 | Pronovost et al. |
| 5,846,835 A | 12/1998 | Sisbarro et al. |
| D405,539 S | 2/1999 | Poissant et al. |
| 5,976,895 A * | 11/1999 | Cipkowski .................... 436/518 |
| 6,008,056 A * | 12/1999 | Thieme ................ G01N 33/558 422/417 |
| D431,867 S | 10/2000 | Maynard et al. |
| D432,244 S | 10/2000 | Anderson et al. |
| D438,807 S | 3/2001 | Liu |
| D448,087 S | 9/2001 | Regan |
| 6,306,642 B1 | 10/2001 | Nelson et al. |
| D454,398 S | 3/2002 | Robertson et al. |
| D456,082 S | 4/2002 | Bouse et al. |
| 6,372,515 B1 * | 4/2002 | Casterlin et al. .............. 436/518 |
| 6,451,607 B1 | 9/2002 | Lawrence et al. |
| 6,605,476 B2 | 8/2003 | Kobayashi |
| 6,656,744 B2 | 12/2003 | Pronovost et al. |
| 6,706,539 B2 | 3/2004 | Nelson et al. |
| 6,766,817 B2 | 7/2004 | da Silva |
| D499,813 S | 12/2004 | Wu |
| D500,142 S | 12/2004 | Crisanti et al. |
| 6,844,200 B2 * | 1/2005 | Brock .......................... 436/514 |
| 6,855,561 B2 | 2/2005 | Jerome et al. |
| 6,918,404 B2 | 7/2005 | da Silva |
| 6,924,153 B1 | 8/2005 | Boehringer et al. |
| 7,041,469 B2 | 5/2006 | Lawrence et al. |
| 7,066,586 B2 | 6/2006 | da Silva |
| 7,144,742 B2 | 12/2006 | Boehringer et al. |
| 7,179,657 B2 | 2/2007 | Jerome et al. |
| 7,226,793 B2 | 6/2007 | Jerome et al. |
| 7,244,398 B2 | 7/2007 | Kotary et al. |
| 7,255,832 B2 | 8/2007 | Lawrence et al. |
| 7,285,255 B2 | 10/2007 | Kadlec et al. |
| 7,291,481 B2 | 11/2007 | Lawrence et al. |
| D560,812 S | 1/2008 | Powell et al. |
| 7,344,893 B2 * | 3/2008 | Kirkegaard et al. .......... 436/514 |
| 2002/0150501 A1 * | 10/2002 | Robertson ........ G01N 33/54386 422/430 |
| 2004/0152207 A1 | 8/2004 | Nelson et al. |
| 2005/0227371 A1 | 10/2005 | Gokhan |
| 2006/0078986 A1 | 4/2006 | Ly et al. |
| 2007/0094928 A1 | 5/2007 | Hunter |
| 2007/0111323 A1 | 5/2007 | Jerome et al. |
| 2007/0243630 A1 | 10/2007 | Boehringer et al. |
| 2007/0281370 A1 | 12/2007 | Jerome et al. |
| 2007/0292314 A1 | 12/2007 | Effenhauser et al. |
| 2008/0015531 A1 | 1/2008 | Hird et al. |
| 2008/0262644 A1 | 10/2008 | McLeod |

* cited by examiner

INTEGRATED ASSAY DEVICE AND HOUSING

CROSS-REFERENCE TO RELATED APPLICATIONS

The application claims the benefit of U.S. Provisional Patent Application No. 61/046,789, filed Apr. 21, 2008, which is incorporated by reference herein in its entirety.

TECHNICAL FIELD

A laminated, integrated, analyte assay device and housing is described. The assay device is useful as an inexpensive, disposable assay device for detecting the presence or amount of a particular analyte in a body fluid or other sample.

BACKGROUND

Single-use disposable devices can be used to perform biochemical assays as in the case, for example, of home pregnancy tests, glucose monitoring tests, drug tests, and numerous other device that allow medical or non-medical persons to perform biochemical assays for detecting various target molecules (or analytes). These assays often utilize antibodies, fluorescent or calorimetric substrates, or other specialized reagents, which can be immobilized on a surface in the device, such as an assay strip, which is typically housed in a cast, extruded or compression-molded rigid plastic housing.

While single-use disposable devices are of great benefit in performing biochemical assays quickly and in the field, they can be difficult to manufacture inexpensively while maintaining consistent quality and functionality. By way of example, frequently such assay strip devices are assembled by hand, presenting significant opportunity for both error in the assembly process and injury to personnel (such as repetitive motion injury). Additionally, such plastic-housed assay strip devices represent yet another source of plastic waste for disposal. For these and other reasons, the need exists for more efficient, cost effective, and environmentally-friendly devices for performing rapid biochemical assays.

The foregoing examples of the related art and limitations related therewith are intended to be illustrative and not exclusive. Other limitations of the related art will become apparent to those of skill in the art upon a reading of the specification and a study of the drawings.

SUMMARY

The following aspects and embodiments thereof described and illustrated below are meant to be exemplary and illustrative, not limiting in scope.

In one aspect, a laminated analyte assay device is provided. The laminated device is comprised of a support strip having a top surface and a bottom surface, an overlamina having a bottom surface in contact with the top surface of the support strip for forming a reservoir between the support strip and the overlamina, and an assay strip comprising at least one reagent for detecting an analyte present in a sample. The assay strip is preferably positioned in the reservoir formed between the support strip and the overlamina and is in fluid communication with an opening in the overlamina for applying a sample suspected of comprising an analyte.

In one embodiment, upon introduction of the sample to the opening for receiving a sample in the overlamina, the sample contacts the at least one reagent for detecting the analyte on the test strip, to thereby detect the presence and/or absence of the analyte, the detecting being visible through the overlamina.

In some embodiments, the overlamina further includes an opening for viewing at least a portion of the assay strip.

In particular embodiments, the opening for receiving a sample in the overlamina and the opening for viewing at least a portion of the assay strip in the overlamina are different openings. In particular embodiments, the overlamina comprises an impermeable transparent member covering the opening for viewing at least a portion of the assay strip. In particular embodiments, the opening for receiving a sample in the overlamina and the opening for viewing at least a portion of the assay strip in the overlamina are the same opening. In particular embodiments, the overlamina is transparent.

In some embodiments, the top surface of the support strip and bottom surface of the overlamina are held in contact with a pressure-sensitive adhesive.

In some embodiments, the support strip is made of a non-heat-sealable material. In particular embodiments, the support strip is made of paperboard.

In some embodiments, the support strip is embossed to increase its rigidity. In some embodiments, the support strip is embossed to form a recess to increase the volume of the reservoir and at least partially contain the assay strip.

In some embodiments, the overlamina is made of a non-heat-sealable material. In particular embodiments, the overlamina is made of paperboard.

In some embodiments, the overlamina is embossed to form a well at the opening for receiving a sample. In some embodiments, the overlamina is embossed to form a recess to increase the volume of the reservoir and at least partially contain the assay strip.

In some embodiments, the assay strip is a lateral flow assay strip.

In some embodiments, the reservoir further comprises a desiccant.

In some embodiments, the assay strip further comprises a lamina of desiccant.

In, some embodiments, the device further comprises, between the support strip and overlamina, a middle lamina having a first surface and a second surface, a thickness, and an interior opening, the first surface being in contact with the top surface of the support strip and the second surface being in contact with the bottom surface of the overlamina, and the interior opening of the middle lamina defining boundaries of the reservoir.

In some embodiments, the thickness of the middle lamina is at least the thickness of the assay strip.

In another aspect, a laminated analyte assay device is provided, comprising (a) a support strip having a top surface and a bottom surface; (b) a middle lamina having a first surface and a second surface, a thickness, and an interior opening, the first surface being in contact with the top surface of the support strip; (c) an assay strip comprising at least one reagent for detecting an analyte, and being disposed in the interior opening of the middle lamina, and further being in contact with the top surface of the support strip, the assay strip having a thickness that is equal to or less than the thickness of the middle lamina; and (d) an overlamina having a bottom surface in contact with the second surface of the middle lamina, and a top surface, the overlamina having an opening for receiving a sample suspected of comprising the analyte and an opening positioned for viewing at least a portion of the assay strip. Upon assembly of the device, the support strip and overlamina define a reservoir bounded by the interior opening of the middle lamina, the reservoir comprising the assay strip, and wherein the opening for receiving a sample in the overlamina is in fluid communication with the reservoir and the opening for viewing at least a portion of the assay strip is adjacent to the at least one reagent of the assay strip.

In one embodiment, upon introduction of a sample to the opening for receiving a sample in the overlamina, the sample contacts the at least one reagent for detecting an analyte on the test strip, thereby detecting the presence and/or absence of the analyte, the detecting being visualized through the opening in the overlamina for viewing at least a portion of the assay strip.

In some embodiments, the middle lamina is foam.

In some embodiments, the interior opening in the middle lamina is die-cut.

In some embodiments, the top surface of the support strip and first surface of the middle lamina are held in contact with a pressure-sensitive adhesive.

In some embodiments, the second surface of the middle lamina and bottom surface of the overlamina are held in contact with pressure-sensitive adhesive.

In some embodiments, any of the described devices are manufactured using a reel-to-reel process.

In some embodiments, any of the described devices are packaged in a foil pouch adhered to the bottom surface of the support strip or top surface of the overlamina.

In another aspect, a method for manufacture of a laminated immunoassay device is provided. The method comprises providing a continuous roll of a support lamina having a top surface and a continuous roll of an overlamina having a top surface and a bottom surface; placing the roll of support lamina and the roll of overlamina on a machine; bringing the bottom surface of the overlamina in contact with the top surface of the support lamina in a continuous process on the machine such that the surfaces affix to one another to form a recess; and inserting an immunoassay test strip into the recess during or prior to affixing the surfaces, thus forming a continuous roll comprising a plurality of laminated immunoassay devices.

In one embodiment, the bottom surface of said overlamina comprises an adhesive. In another embodiment, the top surface of said support lamina comprises an adhesive.

In yet another embodiment, the overlamina is embossed to define a cavity therein. In another embodiment, the support lamina is embossed to define a cavity therein.

In another embodiment, the step of inserting comprises adhering an immunoassay test strip to the cavity of the overlamina. Alternatively, the step of inserting comprises adhering an immunoassay test strip to the cavity of the support lamina.

In another embodiment, the method further comprising collecting the continuous roll comprising a plurality of laminated immunoassay devices on a take-up reel, and cutting the plurality of laminated immunoassay devices into individual laminated immunoassay devices.

Additional embodiments of the present methods, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present methods and compositions. Additional aspects and advantages are set forth in the following description and claims, particularly when considered in conjunction with the accompanying examples and drawings.

DETAILED DESCRIPTION

I. Overview

Figure 1:
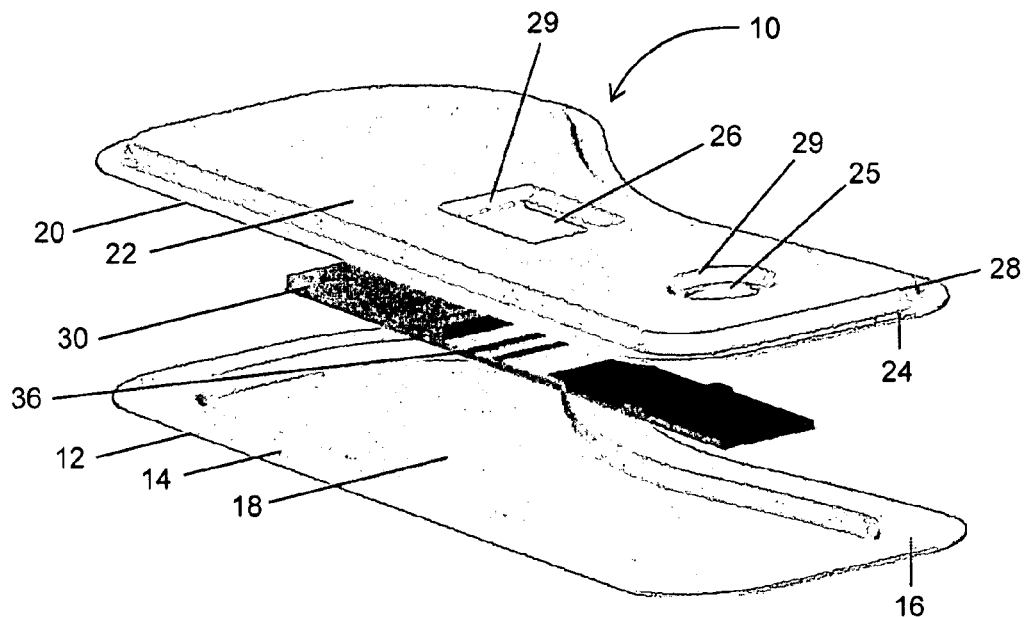
FIG. 1 shows an aspect view of an exemplary two-layer laminated analyte assay device having a stylized shape.

The device described herein is for detecting the presence and/or amount of (i.e., assaying) one or more analytes in a sample. The assay device features a housing formed from as few as two layers of material, which includes a support strip and an overlamina with an opening for receiving a sample for testing for the presence or amount of an analyte. These layers are bonded together to form a laminated analyte assay device housing, which includes a reservoir for containing an assay strip having one or more reagents for detecting the analyte.

II. Definitions

The following definitions are provided for clarity. Words and terms not defined should be accorded their ordinary meaning as use in the art. Note that the single articles "a," "an," and "the" encompass the plural, unless otherwise specified.

As used herein, an "analyte" is any substance that can be detected in a sample, including but not limited to an antigen, immunogen, protein, enzyme, drug or drug metabolite, nucleic acid, carbohydrate, lipid, organism, or other biological molecule.

As used herein, "detecting an analyte" refers to contacting the analyte with one or more reagents to produce a detectable signal that can be observed, directly or indirectly, by an end user. Exemplary detectable signals include, but are not limited to, calorimetric, fluorescent and/or radioactive signals. The described assays may be qualitative or quantitative. In particular embodiments the assays are configured to detect the presence or absence of an analyte, or substantial differences between the relative amounts of analyte, in different samples.

As used herein, a "non-heat-sealable material" is a material that cannot be bonded to itself or another material using heat. Exemplary non-heat-sealable materials are paper products. Thermoplastic materials are generally heat-sealable materials.

As used herein, "disposed in" mean located, positioned, or provided in.

As used herein, reference to a "laminated" device intends two or more layers, or laminae, bonded, compressed or sealed together to form a unitary device. In contrast to devices having a rigid casing or housing that snap-fits together and contains a lateral flow assay test strip, the laminated devices herein, in preferred embodiments, do not snap-fit together, but rather are comprised of bonded layers, wherein two of the layers form a housing that contains a assay test strip. Laminated devices such as those described herein can be produced in a reel-to-reel manufacturing line, and do not require casting or extrusion or insertion of a test strip into a rigid housing that is manufactured, such as by compression molding.

As used herein, "foam" refers to an open or closed cell expanded material. The material is typically expanded using air, although inert gases can also be used.

III. Laminated Analyte Assay Device

Embodiments of the present laminated analyte assay device include at least two layers, or at least three layers, of materials laminated together. In one embodiment, the device is comprised of two layer that include a support strip and an overlamina, which together form a housing for containing an assay strip. Additional layers can be added to provide functionality but are not required to perform the assay. In another embodiment, a device is comprised of three layers that include a support strip, a middle lamina, and an overlamina, which together form a housing for containing an assay strip. Additional layers can be added to provide further functionality but are not required to perform the assay. These embodiments are described in more detail hereinbelow.

In the following description, headings are used to assist the reader but the contents of different sections of the text are not intended to be read in isolation. The same part numbers are used to identify equivalent structures in each Figure, although the particular structures may differ, as described in the text. Some features of the laminated analyte assay device are present in both two-layer embodiments and three-layer embodiments, while other features apply to a particular embodiment. Such features will be made apparent.

A. Support Strip and Overlamina

Figure 2A:
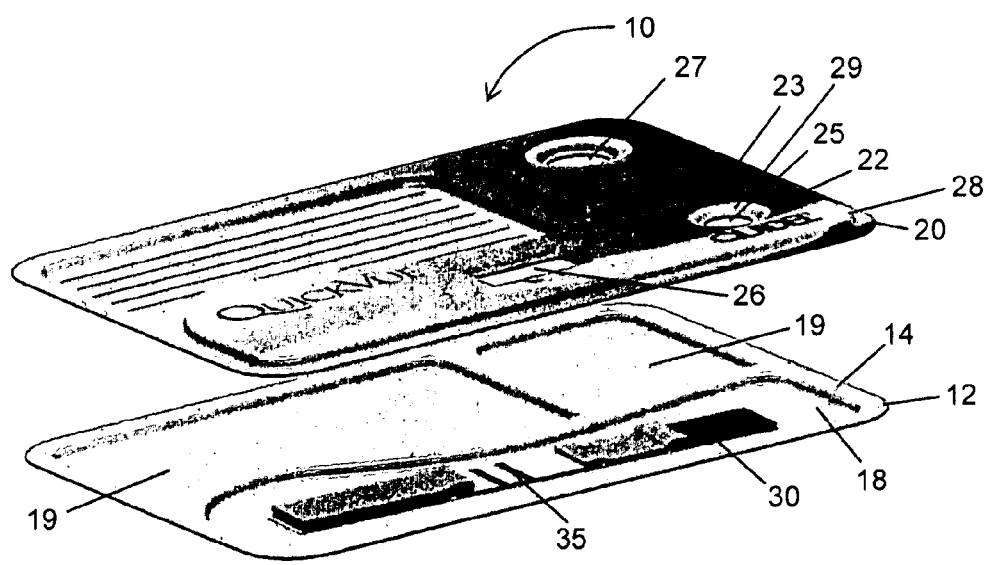
FIG. 2A shows an aspect view of an exemplary two-layer laminated analyte assay device in a form resembling a credit card.
Figure 2B:
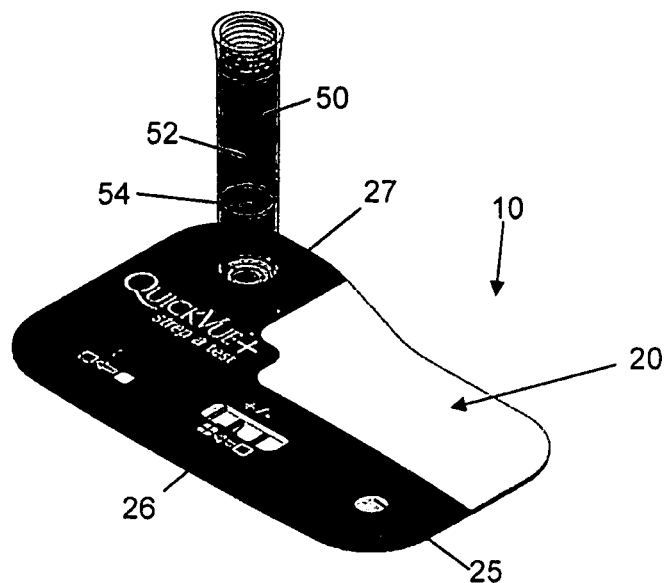
FIG. 2B shows an aspect view of an exemplary laminated assay device including a port for insertion of a tube to form a reservoir.
Figure 2C:
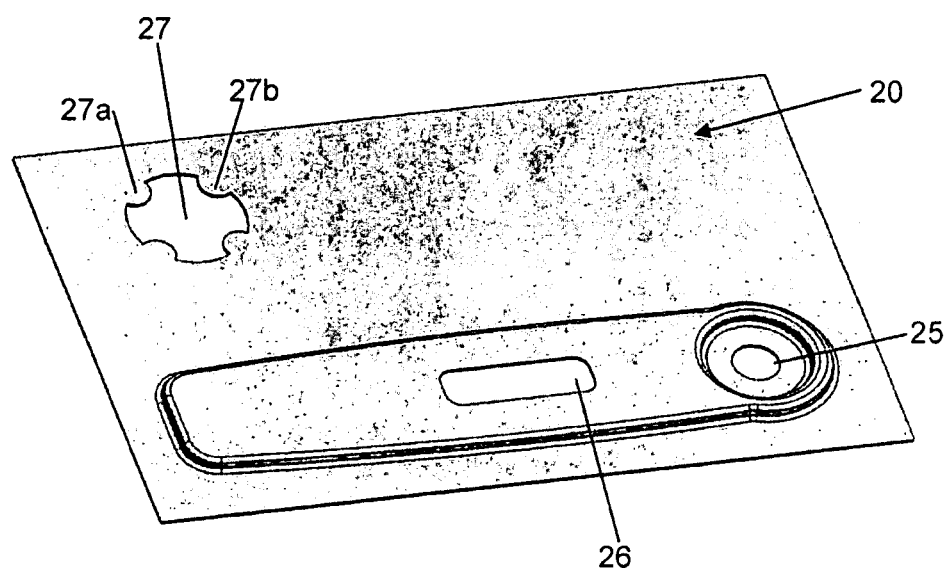
FIG. 2C shows an aspect view of an overlamina having various openings for accessing an assay test strip or for forming a well or reservoir.
Figure 3:
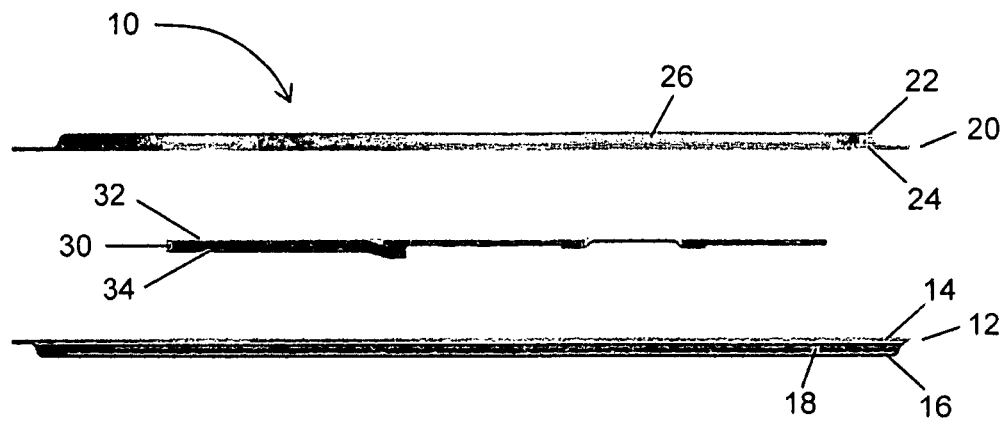
FIG. 3 shows a side profile view of an exemplary two-layer laminated analyte assay device.

Referring initially to FIGS. 1-3, a laminated, analyte assay device 10 includes a support strip 12, or backing layer, having a top surface 14 and a bottom surface 16. Device 10 further includes an overlamina 20 having a top surface 22 and a bottom surface 24. Bottom surface 16 of support strip 12 and bottom surface 24 of the overlamina, best seen in FIG. 3, in one embodiment, lack a wall or a peripheral edge perpendicular to the bottom surface or top surface, such that when the lamina are brought into contact the two surfaces contact one another. In the case of a two-layer structure, top surface 14 of support strip 12 is in contact with bottom surface 24 of overlamina 20. In the case of a three-layer embodiment, a middle lamina (to be described) is interposed between support strip 12 and overlamina 20.

Support strip 12 may be made of any of a variety of materials, including polymers such as polyvinylchloride (PVC), poly(ethylene terephthalate) glycol (PETG), polyvinyl fluoride (PVF), polycarbonate (PC), and paper products, such as paperboard. Additional materials for use in making the support strip are further described, below. The support strip may also be embossed, ribbed, or textured to increase its rigidity, facilitate handling with gloved or wet hands, to provide stability on a flat surface, to add recesses or reservoirs, or otherwise add functionality. One particular embossed pattern provides a recess 18 having sufficient depth to at least partially contain an assay strip 30, which is to be described. The depth of recess 18 refers to its offset with respect to top surface 14 of support strip 12.

Another particular embossed pattern provides a slightly elevated sealing surface, or bead (not shown) on top surface 14 of support layer 12 and/or bottom surface 24 of overlamina 20 to improve sealing once assembled. Another embossed pattern provides additional recesses 19 in support strip 12 (FIG. 2). Another embossed pattern provides "feet" (not shown) on bottom surface 16 of support strip 12 for contacting a tabletop or similar work surface. Yet another embossed pattern provides a company logo, instructions for performing the assay or interpreting the results, disposal or recycling of the assay, emergency information, and the like. Bottom surface 16 of the support strip may also be printed with such instructions or information.

In one embodiment, the support strip of the present device need not be made of a heat-sealable material. Thus the present laminated analyte assay device may expressly utilize a support strip made of a non-heat-sealable material, such as a non-heat-sealable polymer, paper product, or other material identified herein or known in the art. The thickness of the support strip is not critical but is generally less than about 5 millimeters (mm), less than about 4 mm, less than about 3 mm, less than about 2 mm, or even less than about 1 mm.

With continued reference to FIGS. 1-3, overlamina 20 is now described in more detail. As above, overlamina 20 includes a top surface 22 and a bottom surface 24. Depending on the embodiment, the bottom surface may be in contact with top surface 14 of the support strip 12 and/or a middle lamina, as will be described below. Contact between these surfaces can include contact only about the outer periphery of the surfaces or contact across the entire surface, other than any embossed region which forms a cavity or recess there between. Overlamina 20 includes at least one opening 25 for receiving a sample suspected of containing an analyte of interest, the opening being in fluid communication with the assay strip 30, and more specifically in fluid communication with a sample receiving portion of the assay test strip. Overlamina 20 may also include an second opening 26 for viewing at least a portion of the assay strip, preferably the second window is positioned for viewing the portion of the assay strip that includes a reagent for detecting a preselected analyte. In this manner, detection of the analyte can be visualized through the opening 26 in overlamina 20. In various embodiments, the opening in overlamina 20 for receiving a sample and the second opening in overlamina 20 for viewing at least a portion of the assay strip may be the same or different openings.

Figure 4:
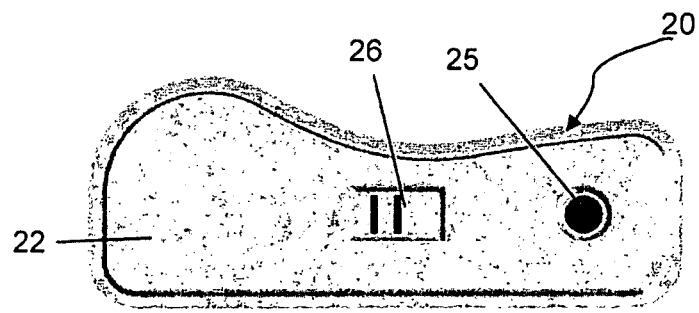
FIG. 4 shows a plan view of an exemplary overlamina having one opening for applying sample and a separate opening for viewing a portion of the assay strip.
Figure 5:
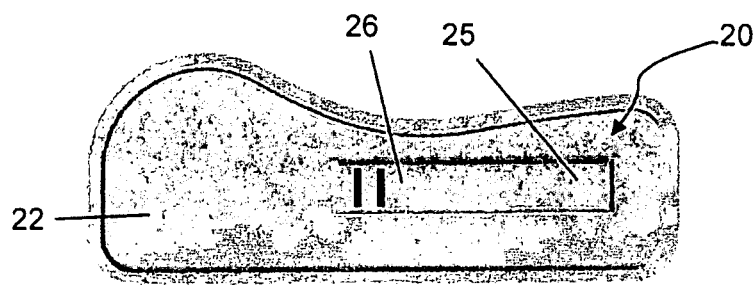
FIG. 5 shows a plan view of an exemplary overlamina having a common opening for applying sample and viewing a portion of the same or different assay strip.
Figure 6:
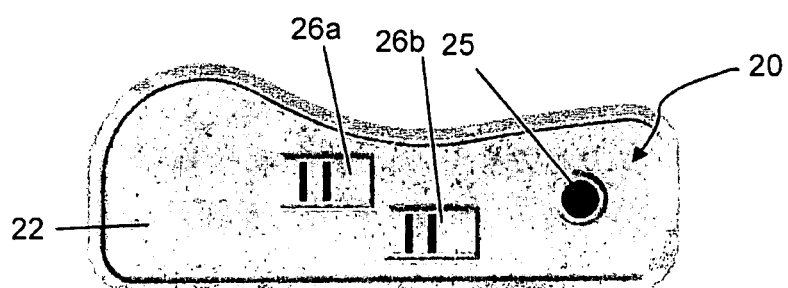
FIG. 6 shows a plan view of an exemplary overlamina having one opening for applying sample and a plurality of separate openings for viewing a portion of one or more assay strips.

FIGS. 4-7 additional embodiments of a laminated device, wherein the top surface 22 of overlamina 20 includes additional optional features. FIG. 4 shows an embodiment similar to that shown in FIGS. 1 and 2, wherein separate openings for receiving a sample and for visualizing the assay strip are present. In the embodiment shown in FIG. 5, the openings 25, 26 for receiving a sample and for visualizing the assay strip, respectively, form a single opening. The device in the embodiment shown in FIG. 6 includes a plurality of openings 26a, 26b, for viewing different portions of the same assay strips, or of different assay strips, which is particularly advantageous when using a laminated analyte assay device for performing several assays simultaneously. In this embodiment wherein a laminated device comprises more than one assay test strip, it is contemplated that test strips can be positioned side by side, such that a test result from a first strip is visible in a first viewing window, and a test result from a second strip is visible in a second viewing window, such as windows 26a, 26b of FIG. 6. The device can include a single opening for receiving a sample, or two openings for receiving two of the same or different samples. The different samples can be two samples from the same patient, such as a saliva sample and a blood sample, or a urine sample and a throat swab, or can be two samples from different patients. A laminated device comprising two assay test strips in a back-to-back arrangement is also contemplated. In this embodiment, an overlamina on an upper side of the device provides an opening for receiving a first sample for detection of a first analyte on a first test strip, and the lamina (which can be a second overlamina) on the opposing side of the device provides a second opening for receiving a sample (which can be the same as the first sample or can be a second, different sample) for detection of a second analyte on the second test strip. For example, a laminated device having a two immunoassay test strips for detection of two analytes in a sample can be a first test strip that detects for influenza A and/or B and a second test strip that detects for Strep A, infections mononucleosis, or the like. The overlamina when in contact with an opposing lamina forms a recess for holding the two test strips. The test strips are placed in the recess such that the bottom surfaces of a first test strip is in contact with the bottom surface of a second test strip, such that the upper surfaces of the test strips are in contact with the overlamina and opposing lamina. In this way, the upper surfaces of the test strips are accessible through one or more openings in the laminae.

Figure 7:
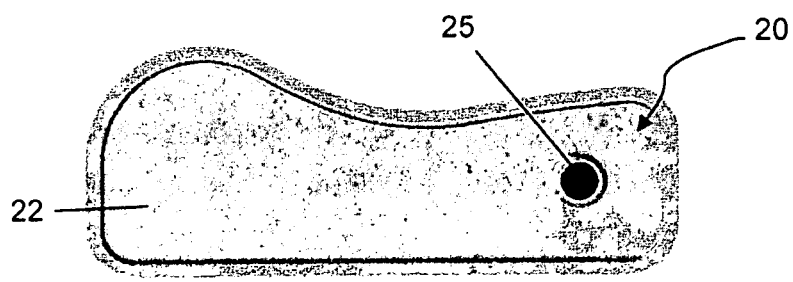
FIG. 7 shows a plan view of an exemplary transparent overlamina having an opening for applying sample but lacking an opening for viewing a portion of the assay strip.

The embodiment shown in FIG. 7 lacks an opening for viewing the assay strip, which may be desirable when the overlamina is made of a transparent material, as is contemplated for any of the device embodiments described herein.

With reference again to FIG. 2A, the device shown in this embodiment includes another opening 27, which may be used to mix a sample with a reagent provided in another part of the device, e.g., prior to introducing the sample to the sample opening 25. Such a reagent may be a dry reagent, and may be contained within a recess 23 in overlamina 20 or recess 19 in the support strip 12. In the embodiment illustrated in FIG. 2B, a tube 50 is removably inserted into opening 27 to form a reservoir 52. The reservoir provides an "on-board" means, for example, for mixing a sample with a reagent contained within opening 27 or for mixing a reagent for placement in the sample opening. The tube may include one or more markings, such as marking 54, to delineate an milliliter amount to facilitate preparation of a solution with a specific concentration of a reagent or a solution with a specific dilution factor.

FIG. 2C illustrates an overlamina 20 comprising openings 25, 26, 27. Opening 27 comprises a plurality of tabs, such as tabs 27a, 27b, that secure a tube or other device to the overlaminae. In one embodiment, it is contemplated that opening 27 aligns with a similar opening in an underlaying support lamina, to provide an opening in the laminated device. A tube or other device with a flange on one end can be inserted into the opening, such that the flange serves as a stop for a liquid tight seal between the tube and the device, to form a reservoir for mixing or storing a sample.

It will be appreciated that in the embodiments of FIGS. 3-7, the openings 25, 26, 27 in the overlamina may be die-cut, machined, melted, or otherwise formed.

The overlamina in the foregoing embodiments may be made from a variety of materials, including polymers such as polyvinylchloride (PVC), poly(ethylene terephthalate) glycol (PETG), polyvinyl fluoride (PVF), polycarbonate (PC), and paper products, such as paperboard. Materials for use in making the overlamina are further described, below. In particular embodiments, the overlamina is made of a transparent material, in which case an opening for viewing the assay strip is not required (FIG. 7).

The overlamina may be embossed, ribbed, or textured to increase its rigidity, facilitate handling with gloved or wet hands, or otherwise add functionality. One particular embossed pattern provides a recess having sufficient depth to at least partially contain the assay strip. Other recesses may be provided, e.g., for containing a desiccant or other reagent. Another particular embossed pattern provides tapered edges, such as edges 29 in FIG. 2A, around the sample opening 25, thereby forming a sample well having a preselected volume. Typical samples volumes for applying to the opening (or well) are from about 5 µL to about 500, µL, about 10 µL to about 400 µL, about 20 µL to about 300 µL, about 40 µL to about 200 µL, about 50 µL to about 150 µL, and the like. Tapered edges may also be provided around the opening for viewing the assay strip. Other embossed patterns provide a company logo, instructions for performing the assay or interpreting the results, disposal or recycling of the assay, emergency information, and the like and the like. Where desired, the processes of embossing and die-cutting can be combined in a single step.

The thickness of overlamina is not critical but is generally less than about 3 mm, less than about 2.5 mm, less than about 2 mm, less than about 1.5 mm, less than about 1 mm, less than about 0.8 mm, less than about 0.6 mm, or even less than about 0.5 mm. The overlamina may be printed, decorated, branded, or otherwise marked to provide information about the laminated analyte assay device or particular assay. Where the overlamina is made of a clear material, such printing may be on the bottom surface of the overlamina.

B. Assay Strip

With continued reference to FIGS. 1-3, the laminated analyte assay device 10 includes one or more assay strips 30 for detecting an analyte. The one or more assay strips are placed between the support lamina and the overlamina. Although not shown in the diagrams, the assay strip may include a laminated layer of desiccant (described in greater detail, below).

Assay strip 30 includes a top surface 32 and a bottom surface 34 (best seen in FIG. 3), and one or more reagents 36 for detecting an analyte, depending on the particular assay for which the laminated analyte assay device is used. The assay strip can be of any format known in the art; however, lateral flow assay strips are preferred. Examples of lateral flow immunoassay devices are described, for example, in U.S. Pat. Nos. 5,766,961; 6,656,744; 6,924,153, which are incorporated by reference herein. Typically, lateral flow assay strips are comprised of overlapping (i.e., in fluid communication), porous portions forming a flow path for the sample from the sample application site (for example, a sample pad) through a label zone (e.g., label pad comprising a mobilizable reagent) to a test zone (comprising, for example, an immobilized capture reagent) and control zone and ending in an absorbent sink. The assay strip may be of any shape or size but is typically rectangular. Some laminated analyte assay devices include a single assay strip, which may include reagents for detecting one or more analytes. Other laminated analyte assay devices include two or more assay strips, which can be placed between a common support strip and overlamina, or placed in a back-to-back arrangement as described above. Each of the two or more assay strips may include reagents for detecting one or more analytes.

The thickness of the assay strip is not critical but is a design consideration when selecting housing dimensions. Exemplary thickness for the assay strip are less than about 5 mm, less than about 4 mm, less than about 3 mm, less than about 2 mm, or even less than about 1 mm. In the two-layer embodiment, the assay strip is placed in the reservoir formed by the recess in the support strip and/or the recess in overlamina. Note that only the support strip, or only overlamina, are required to have such recesses, although both layers may have recesses. In the three-layer embodiment, the assay strip is placed in the reservoir formed in an interior opening of a middle lamina (to be described), which is further bounded by the support strip and overlamina. The reservoir may be increased in dimension by using a support strip and/or an overlamina with a recess. As a general rule, the thickness of the assay strip should be less than the combined depths of the recesses, such as recesses 18, 28, in the support strip and/or overlamina, plus the thickness of middle lamina, if present. In this manner, the assay strip fits within the reservoir.

Preferred materials for making the assay strip are hydrophilic materials capable of wicking sample from a sample application portion of the assay strip to the portion of the assay strip that includes one or more reagents for detecting an analyte. Exemplary materials include cellulose materials (e.g., cellulose, cellulose acetate, nitrocellulose, and the like), glass fibers, polysulfone, polyvinylidene difluoride, polyurethane, polyester, cloth, paper, and other porous materials that allow lateral flow. Typically, assay strips are comprised of different pieces of material placed in overlapping relationship on a single non-porous backing material, such as for example, MYLAR™. Exemplary assay strip pieces or portions include a sample pad, a label pad, test pad or portion and absorbent sink. Other materials for use making the assay strip are described, below.

The size and thickness of the assay strip determine the volume of sample required to saturate the assay strip, and therefore the optimum volume of sample that should be applied to the sample opening of the laminated analyte assay device. For example, a 9 mm-wide assay strip requires a sample volume of about 100-150 µL, while a 7 mm-wide assay strip requires a sample volume of about 75-120 µL. Sample volume is not critical to the operation of the device 10, but is a consideration when designing the housing.

C. Middle Lamina

Figure 8:
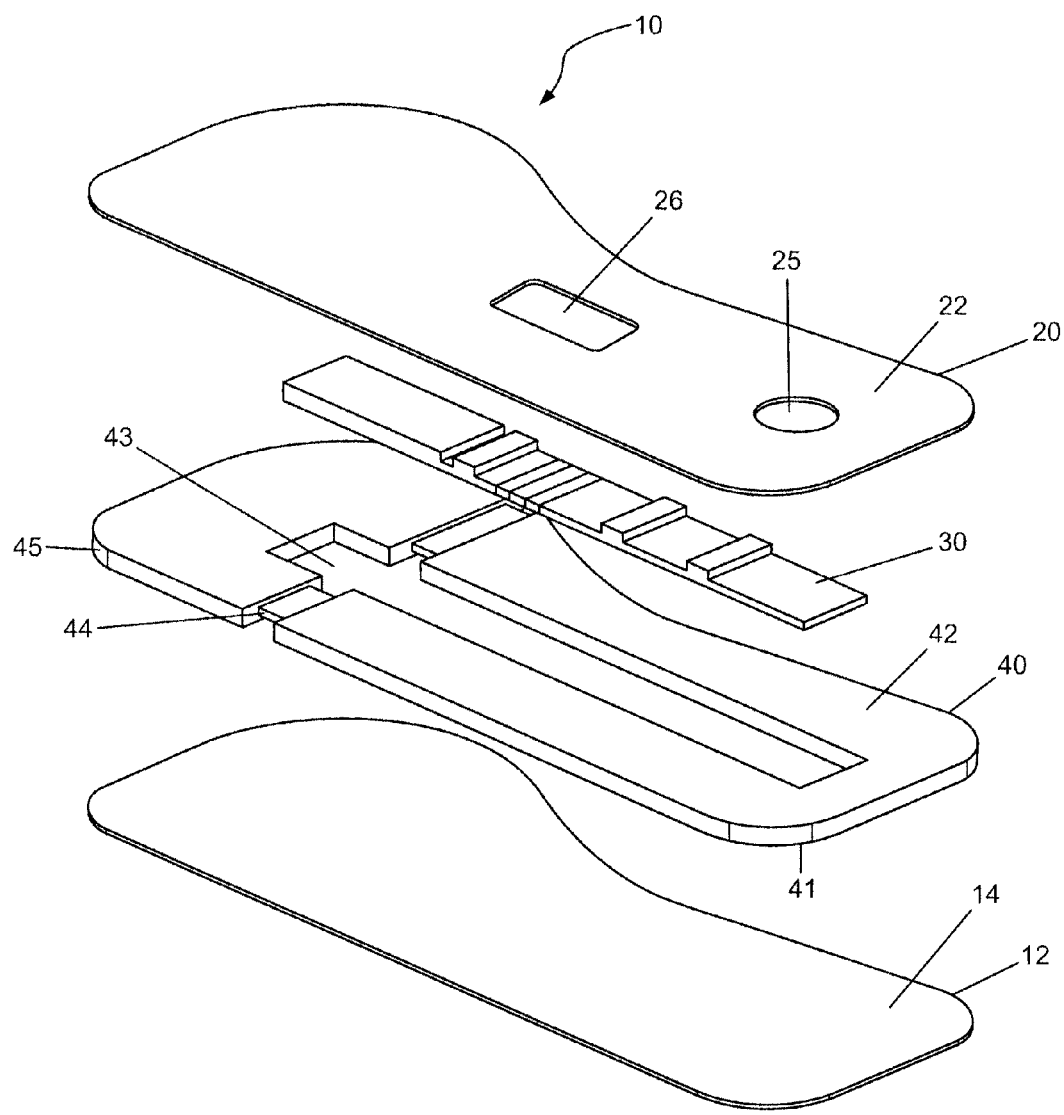
FIG. 8 shows an aspect view of an exemplary three-layer laminated analyte assay device having vents to allow displaced air to escape from the reservoir.
Figure 9:
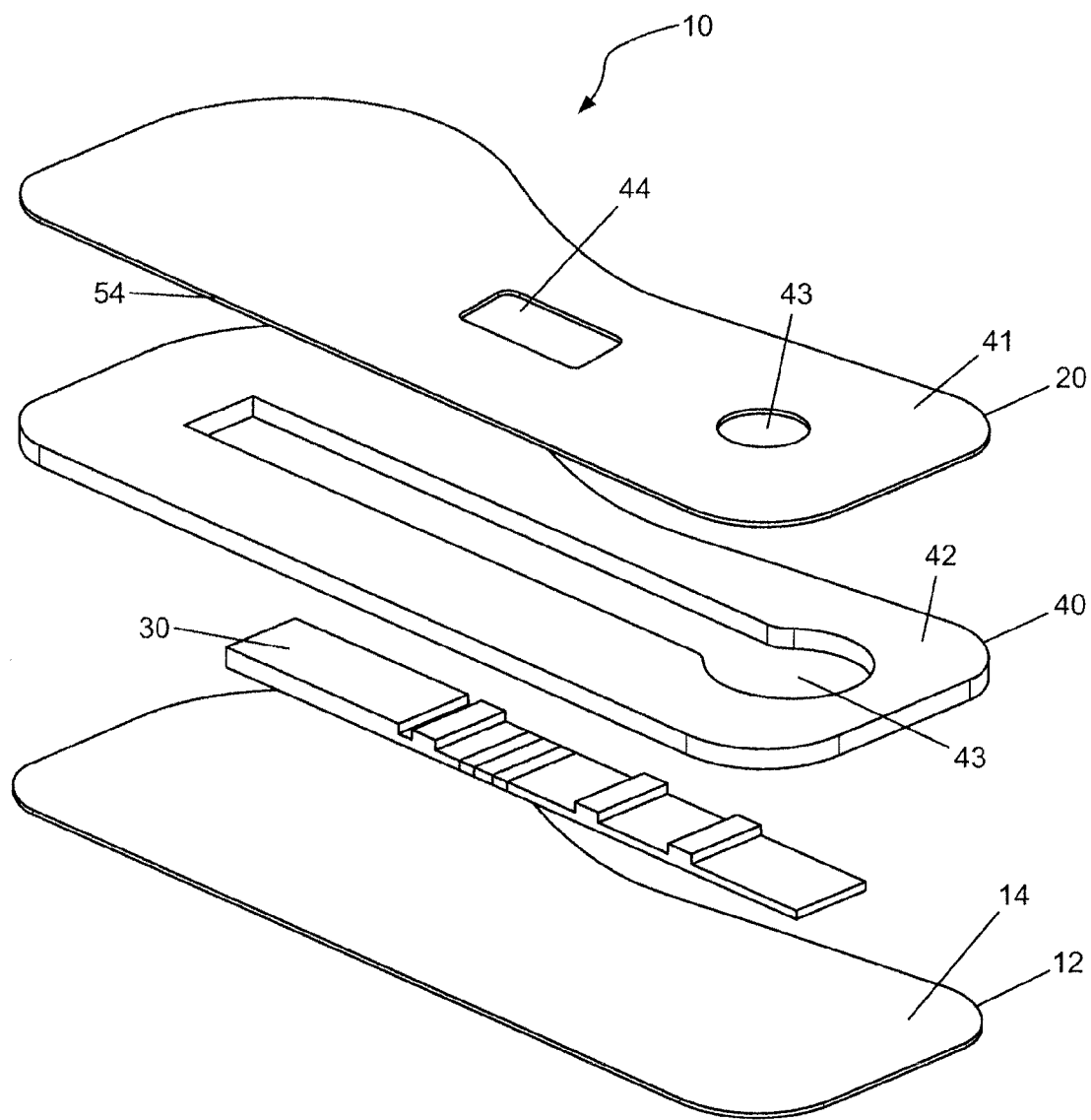
FIG. 9 shows an aspect view of an exemplary three-layer laminated analyte assay device that lacks vents.

As further illustrated in FIGS. 8-9, the laminated analyte assay device 10 may optionally include a middle lamina 40, which serves as spacer between support strip 12 and overlamina 20. This embodiment is referred to as the three-layer embodiment. Whereas support strip 12 and overlamina 20 are in direct contact in the two-layer embodiment, support strip 12 and overlamina 20 are at least partially separated, by the intervening middle lamina 40 in the three-layer embodiment.

Middle lamina 40 has a first surface 41, a second surface 42, and an interior opening 43. The first surface 41 of middle lamina 40 is in contact with the top surface 14 of the support strip 12, while the second surface 42 of middle lamina 40 is in contact with the bottom surface 24 of overlamina 20. Interior opening 43, along with support strip 12 and overlamina 20, define a reservoir in the housing for containing an assay strip 30 within an assembled device 10.

In some embodiments, middle lamina 40 has a thickness that is at least the thickness of test strip 30. The thickness of middle lamina 40 may also be slightly greater than the thickness of a test strip to allow for swelling, e.g., upon wetting with a sample. Where middle lamina 40 has sufficient thickness to provide space for the assay strip, neither the support strip nor overlamina are required to have recesses, although they may be included. Even where a middle lamina is present, it may still be desirable to emboss the support strip to increase rigidity and/or facilitate handling of the laminated assay device, or to emboss overlamina to provide greater rigidity to the laminated assay device and/or to provide tapered edges, e.g., around the sample opening. Accordingly, a three-layer the laminated analyte assay device may include all the features of the two-layer embodiment but further include a middle lamina to increase the space available for the assay strip.

Exemplary thickness values for middle lamina are from about 0.5 to about 5 mm, from about 0.75 to about 4 mm, from about 1 to about 3 mm, and from about 1.25 to about 2.5 mm. The middle lamina may be made of a variety of materials, including those described, herein. Since the middle lamina may have substantially greater thickness than the support strip, overlamina, and/or even the test strip, it may be desirable to use an expanded material, or "foam," such as expanded polystyrene (EPS), polyethylene, cross-linked polyethylene, polyurethane, polypropylene, polyether, coated polyether, polyester, reticulated polyester, neoprene, nitrile, ethylene-propylene-diene-monomer (EPDM), and cork. As above, none of the material for use in the middle lamina need be heat-sealable.

As in the case of the opening(s) in overlamina 20, the interior opening 43 of middle lamina 40 may be die-cut, machined, melted, or otherwise formed. As shown in FIG. 8, interior opening 43 may extend to the peripheral exterior surface 45, such that a channel 44 is formed upon assembly of the laminated analyte assay device. Channel 44 may serve as a vent for allowing air to be displaced from the reservoir upon introduction of the sample. The laminated analyte assay device shown in FIG. 9 does not include channels.

D. Assembly and Operation

With continued reference to the drawings, upon assembly of the laminated analyte assay device, the support strip and overlamina, optionally in combination with a middle lamina, define a reservoir (or internal cavity) for containing an assay test strip. The laminated structure without the assay strip is referred to as the "assay housing," while the addition of the assay strip completes the laminated analyte assay device.

In embodiments of the laminated analyte assay device that require only two lamina, such as the support strip and the overlamina, the top surface of the support strip may be attached to the bottom surface of overlamina using an adhesive. In embodiments of the laminated analyte assay device that require three lamina, the top surface of the support lamina (or support layer) may be attached to the first (i.e., bottom) surface of the middle lamina using an adhesive, and the bottom surface of the overlamina may be attached to the second (i.e., top) surface of the middle lamina using an adhesive. Such adhesives may be the same or different adhesives, and may be applied to the indicated surfaces in any order and in any manner. Examples of adhesives include, but are not limited to cyanoacrylate, epoxy, silicone, rubber cement, putty, mucilage, birdlime, sealant, gum, stickum, and the like. In some embodiments, the adhesive is pressure sensitive. The assay test strip should be positioned in the reservoir during assembly, i.e., prior to the assembling the housing, to avoid the need to insert the assay strip into an assembled housing.

The sample opening in the overlamina is in fluid communication with the reservoir, although it may also be immediately adjacent to the assay strip in the reservoir. In operation, sample is introduced into the opening in the overlamina, to contact the assay test strip that includes at least one reagent for detecting an analyte present in the sample or suspected of being present in the sample. Through liquid flow or wicking action, the sample contacts the one or more reagents on the test strip, producing a detectable change indicative of the presence of the analyte, which is visualized through the opening in overlamina, or through a transparent overlamina material.

Application of the sample displaces air from the reservoir, which may exit via vents in middle lamina (as seen in FIG. 8), the opening in overlamina for applying a sample, the opening in the overlamina for viewing the assay strip, any additional opening in communication with the reservoir, or combinations thereof. Moreover, where a layer of the laminated analyte assay device is made from a porous material, such as paper, venting may be provided directly through the material. Accordingly, venting air from the laminated analyte assay device is generally not an issue.

Keeping the volume of the sample small avoids over-filling the reservoir such that leakage from the device is minimal, even when one or more layers of the device are made of paper or similar materials that are not generally used to contain fluid samples. Because the assay strip is absorbent by design, the applied sample is captured on the assay strip, allowing the used laminated analyte assay device to be disposed of as an essentially "dry" object. Where a sample may include an infectious agent, e.g., hepatitis virus, HIV, influenza virus, and the like, the used laminated analyte assay device may be sprayed or doused with bleach or another suitable disinfectant prior to disposal, or autoclaved, incinerated, or otherwise destroyed.

The laminated analyte assay device is designed to be simple to use and to produce a detectable result that can be interpreted by a medical technician, physician, or lay person. In many cases, the detectable signal is stable for hours or days. The laminated analyte assay device has applications in clinical laboratories, physician's offices, outpatient centers, hospitals, in the field, and over-the-counter.

The laminated assay device may be packaged for individual use, such as in a foil or polymer film pouch. The device may also be packaged in bulk, particularly for application requiring a number of the devices at once. Depending on the form of packaging, a portion of the laminated analyte assay device may adhere to the pouch (e.g., the bottom surface of the support strip or the top surface of the overlamina), or the laminated analyte assay device may be free moving within the pouch. The pouch may be printed with a description of the assay and/or instructions for using the device or interpreting the results.

The present laminated analyte assay devices offer several advantages over conventional laminar flow assays and prepackaged or disposable assays. First, the present device is essentially closed to the external environment, except for the openings in the overlamina and the optional vents in any middle lamina, where present. This prevents the end user from contacting and contaminating the test strip, as can be the case for open laminated test strips, as exemplified by litmus paper. Substantially enclosing the assay strip also increases the stability of the assay reagents before and after adding sample to the laminated analyte assay devices. Second, the laminated analyte assay device can be assembled inexpensively and in quantity using a variety of manufacturing processes, including reel-to-reel manufacturing, as further described below.

Note that the shapes of the laminated analyte assay device shown in the diagrams are exemplary. The present device may be rectangular, oval, kidney-shaped, or any other shape that is convenient for handling, use, brand recognition, and the like.

IV. Manufacturing and Quality Control

A. General Manufacturing

The present laminated analyte assay device can be manufactured by any known manufacturing process. For the purposes of large-scale production, efficiency generally requires that large sheets of material are first bonded together, and then cut into numerous individual devices. Using such methods, the necessary openings and holes in overlamina (and middle lamina, if present) are first formed, and then the sheets with openings and holes are aligned and bonded to form a laminated structure, which is cut into individual laminated analyte assay devices.

For example, a sheet of support strip may include an adhesive top surface, which adhesive surface is brought into contact with the first (bottom) surface of a sheet of middle lamina, and/or the first (bottom) surface of the sheet of middle laminate may include an adhesive surface, which is brought into contact with the top surface of a sheet of the support strip.

Similarly, a sheet of overlamina may include an adhesive bottom surface, which is brought into contact with the second (top) surface of a sheet of middle lamina. Alternatively, a sheet of middle lamina may include an adhesive second (top) surface, which is brought into contact with the bottom surface of a sheet of overlamina.

Unless an opening of sufficient size for inserting an assay strip into the reservoir is formed in one of the layers, the assay strip is preferably introduced before the support layer, any middle lamina (if present), and overlamina are bonded together to form a laminate.

B. Reel-to-Reel Manufacturing

A manufacturing method particularly well suited for making the present laminated analyte assay device is reel-to-reel manufacturing (or processing), which uses a feed reel and a take-up reel to control a manufacturing process that occurs on a carrier strip. The carrier strip to which components are attached for manipulation and assembly may be indexed such that movements are incremental, typically corresponding to the location of different stations along an assembly line. The carrier strip may be a metal, paper, polymer, or composite, and may include a wire or cable to confer structural integrity. The completed or assembled parts or precursors may be delivered to a remote location for further processing while still on the take-up reel or may be removed from the carrier strip for packaging and delivery, for example to an end user or customer. Such manufacturing technology is particularly well suited for laminated assay devices of the present invention, as described further herein.

In the case of the two-layer embodiment, the support strip and overlamina may each be provided as separate continuous rolled sheets, to be laminated during processing. In particular, the top surface of the support strip and the bottom surface of overlamina are brought into contact during manufacturing to produce a two-layer housing, preferably with a strip assay inserted there between prior to lamination. The top surface of the support strip and/or the bottom surface of overlamina may include an adhesive surface as described above. The adhesive surface may be covered with a protective layer, which is removed during manufacturing to expose the adhesive layer.

The assay strip is preferably inserted between the support strip and the overlamina before these layers are brought together. By way of example, the top surface of the support strip may comprise an adhesive covered by a protective layer such that during reel-to-reel manufacturing, the protective layer is removed, exposing the underlying adhesive. The assay strip is then placed on the adhesive, within the embossed recess of the support strip. The top surface of the support strip and bottom surface of the overlamina are then brought into contact with one another, resulting in a continuous sheet of laminated devices. Thereafter, the devices are separated, for example cut, from one another, preferably in an automated assembly process, for individual packaging. Alternatively, where the overlamina includes a slot (not shown), or opening of sufficient size to allow the insertion of an assay strip into the assembled housing, the assay strip may be added after assembling the housing. Similarly, the support strip, rather than the overlamina, may include a slot or opening (not shown) to allow insertion of the assay strip into the assembled housing.

In the case of the three-layer embodiment, the support strip, middle lamina, and the overlamina may each be provided as a separate continuous sheet, to be laminated during processing. Alternatively, the support strip and middle lamina, or middle lamina and the overlamina may be provided as a single layer of material, which is brought into contact with the remaining layer during manufacturing to produce the three-layer housing. The top surface of the support strip, first and/or second surfaces of middle lamina, and/or the bottom surface of the overlamina may include an adhesive surface as described herein. The adhesive surface may be covered with a protective layer, which is removed during manufacturing to expose the adhesive layer.

As with the two layer embodiment, the assay strip is preferably placed on the top surface of the support strip, within the interior opening of middle lamina and then the overlamina brought into contact with the top surface of the support strip and/or top surface of the middle lamina. Alternatively, the overlamina may include a slot or opening of sufficient size to allow the insertion of an assay strip into the assembled housing, the assay strip may be added after assembling the housing. Similarly, instead of an opening within overlamina, the support strip may include a slot or opening to allow insertion of the assay strip into the assembled housing.

C. Lamina Materials

A number of different material can be used to make the various layers of the present laminated analyte assay device. For example, the support strip can be made of polymers such as polyvinylchloride (PVC), polyvinyl fluoride (PVF), rigid vinyl (RPVC), poly(ethylene terephthalate) glycol (PETG), polycarbonate (PC), polyester (e.g., MELINEX®, MYLAR®), polyetherimide (PEI), polypropylene (PP), polystyrene (PS), low density polyethylene (LDPE), high density polyethylene (HDPE), polyimide (PI), acrylic polymethylmethacrylate (PMMA), polyamide (e.g., NYLON® 6 and NYLON® 12), polyethylene naphthalate (PEN), polyurethane, cellulose triacetate (CTA), cellulose acetate butyrate (CAB), and others.

Some polymers, like polycarbonate, polypropylene (PP), and polystyrene (PS), are heat-sealable, while others, like cellulose derivatives, are not; however, heat-sealing is not required to manufacturing the present devices. The support strip may alternatively be made of paper, paperboard, cardboard, posterboard, or a similar paper product, which are non-heat-sealable materials. One or more surfaces of the paper product may have a hydrophilic coating that resists wetting, so long as the coating does not interfere with the assay. Other support materials are known in the art.

The support strip may be embossed, ribbed, or otherwise textured, to increase its rigidity, assist in handling, improve sealing against the middle lamina, or otherwise add functionality. Where the support strip is embossed, it may be preferable to use a material that can be cold formed, to avoid the need for heating. Exemplary materials for cold forming are PVC, PETG, and polyamide. Alternatively, the support strip material, and or the embossing dies, may be heated to improve embossing results using these or other materials. In some embodiments, It may also be preferable to select a material that is not prone to crazing upon molding, to avoid the appearance of stress lines or "whitening" of other wise clear or translucent plastic.

The overlamina may be made from any of the materials for use in making the support strip or middle lamina (if present). In some embodiments, the overlamina is made of an opaque material, while in other embodiments the overlamina is made of a transparent material. The overlamina may be embossed, ribbed, or otherwise textured, to increase its rigidity, facilitate handling, improve sealing against the middle lamina, or otherwise add functionality. The overlamina may also be styled to appeal to the end user and printed with information to assist in performing and interpreting the assay.

When the overlamina is made of a transparent or semi-transparent material, the opening for viewing the portion of the assay strip that includes a reagent for detecting an analyte is optional. Moreover, a semitransparent material that is colored may be used as an optical filter to assist in visualizing the detection of an analyte.

The assay strip is preferably made of a hydrophilic material capable of wicking sample from the point of sample application to reagents for detecting an analyte. Exemplary materials are cellulose materials, such as cellulose (including paper products), cellulose acetate, and nitrocellulose, glass fibers, polysulfone, polyvinylidene difluoride, cloth, and other porous materials. Exemplary paper products are laboratory filter paper and paperboard. Examples of lateral flow immunoassay devices are described, for example, in U.S. Pat. Nos. 5,766,961; 6,656,744; 6,924,153, which are incorporated by reference herein. The assay strip may be of any shape or size but are typically rectangular.

Various features used for enhancing lateral flow assay may be adapted to the laminated analyte assay device, such as those described in U.S. Pat. Nos. 4,943,522, 4,818,677, 5,268,146, 5,223,220, 5,763,262, 6,924,153, 5,766,961, 5,770,460, 6,855,561, 6,451,607, 6,306,642, 7,179,657, 7,255,832, 7,226,793, 7,144,742, 6,706,539, 6,656,744, 5,783,401, 5,741,662, 5,686,315, 5,541,069, 5,521,102, 5,415,994, 5,225,328, and 5,221,616, and U.S. Pat. Pub. Nos. 2007/0243630, 2007/0111323, 2007/0281370, 2006/0078986, 2005/0227371, and 2004/0152207.

When present, a middle lamina may be made of any of the materials for use in making the support strip and the overlamina. In some embodiments, an expanded material, or "foam," is used, which provides increased layer thickness without requiring additional material. The foams may be an open cell foam, a closed cell foam, or a composite, thereof. Exemplary foams are expanded polystyrene (EPS), polyethylene, cross-linked polyethylene, polyurethane, polypropylene, polyether, coated polyether, polyester, reticulated polyester, neoprene, nitrile, and ethylene-propylene-diene-monomer (EPDM). Alternatively, the middle lamina may be made of paperboard, cardboard, posterboard, or a similar paper product, or cork, which are non-heat-sealable materials. One or more surfaces of the paper product may have a hydrophobic coating that resists wetting, so long as the coating does not interfere with the assay. Other support materials are known in the art. The middle lamina may be embossed, ribbed, or otherwise textured, to increase its rigidity, improve sealing against the support strip or the overlamina, or otherwise add functionality.

Material for use in making the laminated analyte assay device may be provided in strips, sheets, or rolls, and may include backing or protective layers, which may be removed prior to assembling the layers.

D. Adhesives

Adhesives for use in assembling the laminated analyte assay device include, but are not limited to epoxy, cyanoacrylate, silicone, putty, rubber cement, mucilage, birdlime, sealant, gum, stickum, and the like. In some embodiments, a pressure-sensitive adhesive (PSA) is used, which forms a bond when pressure is applied. Solvents and heat are not required to activate a PSA, making them well suited for the present application. Exemplary PSA for making the present devices include acrylic, silicone, polyvinyl ether, polyvinyl pyrrolidone, and urethane based adhesive, in addition to natural rubber and polyisobutylene. Material layers coated with PSA may include backing or protective layers, which may be removed prior to assembling the layers.

E. Quality Control

Quality control is important in any manufacturing process. In reel-to-reel manufacturing, cameras are often used to inspect up to 100% of the individual strip-mounted products. The cameras may check a component's or device's surface, shape, position, dimensions, and/or the presence or absence of a critical feature. However, the ability to detect defects does not immediately translate into the ability to discard the defective assemblies of products. Interrupting reel-to-reel manufacturing to remove defective assemblies defeats the purpose of using the high speed process; therefore, defective assemblies often remain on the strip, to be detected and isolated at the end of the manufacturing process. Unfortunately, some defect in an assembly may be difficult to detect in the finished product, particularly where the product consists of a number of layers or subassemblies that are hidden or even physically inaccessible in the final product or component of a product, such as, for example due to lamination of components.

One way to identify defective laminated analyte assay devices or their components manufactured in a reel-to-reel manner is by marking defective devices/components with magnetic ink, which can be detected at a convenient time following manufacturing. The magnetic ink can be detected even if the marked defective part or assembly is concealed, hidden, obscured, or otherwise inaccessible to conventional methods of detection. Detecting defective devices/components using magnetic ink is described in U.S. Publication No. 2008-0262644, which is hereby incorporated by reference.

IX. Biological Samples

The laminated analyte assay device may be used to detect a variety of analytes (or substances) in liquid biological samples, including drugs of abuse, alcohol, therapeutic drugs, micro-organisms, infectious pathogens, bacteria, viruses, fungi, parasites, blood components, antibodies, hapto-hemoglobin complexes, enzymes, proteins, allergens, glucose, creatinine, hormones, tumor markers, cardiac markers, pesticides, explosives, poisons, and environmental pollutants.

Biological samples for use with the laminated analyte assay device 10 include but are not limited to urine, saliva, sputum, mucous, blood, plasma, serum, amniotic fluid, semen, vaginal secretions, tears, spinal fluid, body cavity washings, and other bodily fluids. Other biological samples include samples of food products, animal feed, waste water, drinking water, sewage, soil, dust, and the like.

In addition to identifying microorganisms, the laminated analyte assay device 10 may also be used to type pathogens, such as viruses, bacteria, fungi, or parasites. In one example, the apparatus is used to type flu virus as described in U.S. Pat. No. 5,415,994. Additional exemplary uses for the laminated analyte assay device 10 include but are not limited to detecting trichomonal and other hydrolases, as described in e.g., U.S. Pat. Nos. 7,291,481 and 7,041,469; chlamydia, as described in e.g., U.S. Pat. No. 5,773,234; chorionic gonadotropin, as described in, e.g., U.S. Pat. No. 4,496,654; creatinine, as described in e.g., U.S. Pat. No. 5,804,452; *Helicobacter pylori*, as described in e.g., U.S. Pat. No. 5,846,751; bacterial antigens, as described in e.g., U.S. Pat. No. 5,536,646; fertility and pregnancy, as described in e.g., U.S. Pat. Nos. 5,118,630 and 5,786,220; and sperm motility, as described in, e.g., U.S. Pat. No. 5,434,057. All of these patents are incorporated by reference herein.

X. Assay Reagents

Assay reagents that produce a detectable signal in the presence of an analyte may be in dry or liquid form. Dry assay reagents (including air-dried or lyophilized reagents), generally have a longer shelf life than liquid reagents, and may be preferred in some embodiments. Whether in dry or liquid form, assay reagents may include buffer components, salts, dyes, chaotropic agents, preservatives, reducing agents, and the like.

In some embodiments, the laminated analyte assay device is used to perform an immunoassay, and one of the assay reagents, on or in the assay strip, is an antibody, or fragment or derivative, thereof. Antibody reagents are generally stable for prolonged periods of time in liquid form and in dry form. Antibodies are available for detecting a wide variety of clinically or environmentally relevant substances present in biological samples, and such antibodies need not be described in detail. Antibodies may be used in combination with one or more additional reagents that produce a detectable signal upon binding of the antibody to a target antigen. By way of example, a label reagent comprising an antibody, capable of binding to the analyte of interest, and conjugated to a detectable label, such as a colored particulate label for example, a colored latex bead or metal sol, may be releasably applied to a label pad portion of the assay strip. A second capture reagent, comprising a second antibody, capable of binding the analyte/label reagent compound, is immobilized in the test region of the assay strip such that analyte/label reagent present in the migrating sample is captured. The accumulation of label at the test line then provides a visual signal of the presence of analyte in the sample. Alternatively, labels may be selected that provide a fluorescent or radioactive or magnetic or similar non-visual indication of the presence of analyte in the sample. In such alternative cases, a reader or similar detection means must be employed to detect the presence of signal, if any, at the test line.

In addition to antibodies, other assays reagents include substrates for enzymes present in the sample that produce a colorimetric product, enzymes that catalyze conversion of an analyte in the sample to a detectable product, polynucleotides (e.g., probes) that hybridize to particular nucleic acids in the sample, and the like.

Sample buffer, if present, may further include one or more reagents to disinfect a biological sample or deactivate infectious agents within a biological sample, including but not limited to alcohols, chlorine compounds, phenolic compounds, quaternary ammonium compounds, iodophors, or antibodies, so long as they do not interfere with the assay.

The laminated analyte assay device may further include a desiccant. The desiccant can be integrated into the assay strip, attached to the bottom surface of the overlamina, attached to the top surface of the support strip, or otherwise disposed within the assay device. Where the support strip or the overlamina includes additional recesses, as shown in FIG. 2, desiccant may be placed in such recesses.

In one example, the desiccant is integrated into a film membrane molded piece, for example, a polyethylene film having desiccant dispersed therein. An example of a desiccant in the form of a film or tape is described in U.S. Pat. Nos. 7,005,459 and 6,613,405, and its use in an assay strip is described in U.S. Publication No. 2008-0311002, which are incorporated by reference herein. In this form, the desiccant provides a stable, non-reactive, non-corrosive material that does not leave particulates capable of interfering with performance of the apparatus, as can occur when a desiccant is in a loose form or in a sachet. The desiccant film material may be in contact with the sample, need not be removed prior to use, and does not interfere with performance of the apparatus. The desiccant film may be attached to the assay strip, the support strip, or the overlamina, e.g., using an adhesive. Examples of adhesives include, but are not limited to paste, putty, rubber cement, mucilage, birdlime, sealant, epoxy, and stickum. Exemplary adhesives are silicone, epoxy, or cyanoacrylate-based, although other adhesives, including pressure sensitive adhesives.

Examples of desiccants include, but are not limited to, molecular sieve, alumina, bauxite, anhydrous calcium sulfate, water-absorbing clays, silica gel, zeolite and any of the other moisture-absorbing materials known to the art. Other exemplary desiccants are described in detail in U.S. Pat. Nos. 5,911,937, 6,214,255, 7,005,459, 6,613,405 and 6,130,263, which are incorporated by reference herein.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A laminated analyte assay device, comprising:
    a support strip and
    an overlamina in contact with the support strip, wherein said overlamina is embossed to form one or more recesses between the support strip and the overlamina, and the support strip and overlamina are bonded together at surfaces other than said recesses;
    an assay strip comprising at least one reagent for detecting an analyte present in a sample, the assay strip positioned in one of said one or more recesses, for fluid communication with a sample opening in the overlamina for receiving the sample,
    wherein the overlamina is embossed to form a well or recess at said sample opening, and further includes a separate viewing opening, for viewing at least a portion of the assay strip, and
    the well or recess being sized to hold a preselected volume of a sample, where the preselected volume of sample is sufficient to saturate the assay strip without over-filling the recess that the assay strip is positioned in.

2. The device of claim 1, wherein the overlamina is transparent.

3. The device of claim 1, wherein the support strip and the overlamina are secured in contact at surfaces other than said recesses by a pressure-sensitive adhesive.

4. The device of claim 1, wherein the support strip is made of paperboard.

5. The device of claim 1, wherein the support strip is embossed.

6. The device of claim 1, wherein the overlamina is made of paperboard.

7. The device of claim 1, wherein the assay strip is a lateral flow assay strip.

8. The device of claim 1, further comprising a desiccant, wherein said desiccant is integrated into the assay strip, attached to the bottom surface of the overlamina, attached to the top surface of the support strip, or otherwise disposed within the assay device, in the form of a film membrane having desiccant dispersed therein.

9. The device of claim 1, prepared according to a process of reel-to-reel manufacturing.

10. The device of claim 1, wherein at least one of said support strip and overlamina is embossed to form a further recess which is in fluid communication with a further opening in the overlamina, separate from said sample opening and viewing opening.

11. The device of claim 10, wherein said further opening is adapted to secure a tube that may be removably inserted into said further opening.

12. The device of claim 11, further comprising a tube which is removably inserted into said further opening.

13. The device of claim 12, wherein said tube forms a liquid-tight seal with said further opening.

14. The device of claim 1, wherein the preselected volume of the well or recess is from about 5 µL to about 500 µL.

15. A method for detecting the presence or absence of an analyte in a sample, comprising:
    providing a laminated analyte assay device comprising:
    (i) a support strip,
    (ii) an overlamina in contact with the support strip, wherein said overlamina is embossed to form one or more recesses between the support strip and the overlamina, and the support strip and overlamina are bonded together at surfaces other than said recesses;
    (iii) an assay strip comprising at least one reagent for detecting an analyte present in a sample, the assay strip positioned in one of said one or more recesses, for fluid communication with a sample opening in the overlamina for receiving the sample,
    (iv) wherein the overlamina is embossed to form a well or recess at said sample opening, and further includes a separate viewing opening, for viewing at least a portion of the assay strip, and
    (v) the well or recess being sized to hold a preselected volume for receipt of a sample of a preselected volume, where the preselected volume of sample is sufficient to saturate the assay strip without over-filling the recess that the assay strip is positioned in, and
    introducing a sample to fill the well or recess at the sample opening in the overlamina, whereupon the sample contacts the at least one reagent for detecting an analyte on the assay strip.

16. The method according to claim 15, wherein said detecting is achieved by visual inspection of at least a portion of the assay test strip through said viewing opening in the overlamina.

* * * * *